US007989393B2

(12) United States Patent
Kang et al.

(10) Patent No.: US 7,989,393 B2
(45) Date of Patent: Aug. 2, 2011

(54) METHODS OF CONTROLLING ALGAE WITH THAXTOMIN AND THAXTOMIN COMPOSITIONS

(75) Inventors: Yaowei Kang, Blacksburg, VA (US); Shawn Semones, Salem, VA (US); Jonathan Leder, Roanoke, VA (US); Anh Tran, Roanoke, VA (US)

(73) Assignee: Novosymes Biologicals, Inc., Salem, VA (US)

( * ) Notice: Subject to any disclaimer, the term of this patent is extended or adjusted under 35 U.S.C. 154(b) by 723 days.

(21) Appl. No.: 12/098,694

(22) Filed: Apr. 7, 2008

(65) Prior Publication Data

US 2008/0248956 A1 Oct. 9, 2008

Related U.S. Application Data

(60) Provisional application No. 60/910,723, filed on Apr. 9, 2007.

(51) Int. Cl.
*A01N 43/60* (2006.01)
*A01N 43/34* (2006.01)
*A01N 25/00* (2006.01)

(52) U.S. Cl. ......................... 504/155; 504/136; 424/405

(58) Field of Classification Search .................. 504/155, 504/136

See application file for complete search history.

(56) References Cited

U.S. PATENT DOCUMENTS 5,407,899 A 4/1995 Howell

FOREIGN PATENT DOCUMENTS

CA 2205976 5/1997
WO WO 01/56386 8/2001

OTHER PUBLICATIONS

King et al., "Herbicidal Properties of the Thaxtomin Group of Phytotoxins", J. Agric. Food Chem., vol. 49, No. 5, pp. 2298-2301 (2001).
King et al., "Isolation and Identification of Pigments Generated in vitro by *Streptomyces acidiscabies*", J. Agric. Food Chem., vol. 44, pp. 2849-2851 (1996).
Goyer et al., "Pathogenicity of *Streptomyces scabies* Mutants Altered in Thaxtomin A Production", Phytopathotogy, vol. 88, No. 5, pp. 442-445 (1998).
Healy et al., "The txtAB genes of the plant pathogen *Streptomyces acidiscabies* encode a peptide synthease required for phytotoxin thaxtomin A production and pathogenicity", Molecular Microbiology, vol. 38, No. 4, pp. 794-804 (2000).
Miyajima et al., "*Streptomyces turgidiscabies* sp. nov." International Journal of Systematic Bacteriology, vol. 48, pp. 495-502 (1998).
Natsume et al., "Phytotoxin Production and Aerial Mycelium Formation by *Streptomyces scabies* and *S. acidiscabies* in Vitro", J. Gen. Plant Pathol., vol. 67, pp. 299-302 (2001).
King et al., "Microbial Glucosylation of Thaxtomin A, a Partial Detoxification", J. Agric. Food Chem., vol. 48, No. 2, pp. 512-514 (2000).
Scheible et al., "An Arabidopsis Mutant Resistant to Thaxtomin A, a Cellulose Synthesis Inhibitor from *Streptomyces* Species", The Plant Cell, vol. 15, pp. 1781-1794 (2003).
Simpson et al., "The real kingdoms of eukaryotes" Current Biology, vol. 14, No. 17, pp. 693-696.
Loria et al., "Evolution of Plant Pathogenicity in *Streptomyces*", Annu.Rev. Phytopathol, vol. 44, pp. 469-487 (2006).
Doumbou et al., "Selection and Characterization of Microorganisms Utilizing Phytotoxin Produced by *Streptomyces scabies*", Appl Environ Microbiol., vol. 64, pt 11, pp. 4313-4316 (1998).
Doumbou et al, Applied Environment Microbiol, vol. 64, No. 11, pp. 4313-4316 (1998).
Ioannes Tsekos , J. Phycol, vol. 35, pp. 635-655 (1999).

*Primary Examiner* — Johann R Richter
*Assistant Examiner* — Mei-Ping Chui
(74) *Attorney, Agent, or Firm* — Thomas C. Sova, IV.

(57) ABSTRACT

Methods of treating and/or controlling algae including contacting algae with an effective amount of one or more thaxtomins are disclosed. One or more thaxtomins are applied to algae contaminated environments in a predetermined amount effective in controlling, reducing and/or killing algae.

17 Claims, No Drawings

METHODS OF CONTROLLING ALGAE WITH THAXTOMIN AND THAXTOMIN COMPOSITIONS

CROSS-REFERENCE TO RELATED APPLICATIONS

This application claims priority or the benefit under 35 U.S.C. 119 of U.S. provisional application No. 60/910,723 filed Apr. 9, 2007, the contents of which are fully incorporated herein by reference.

BACKGROUND

1. Technical Field

This disclosure relates to treating algae with one or more thaxtomins. The methods are useful for application to water such as raw water, or algae contaminated surfaces or equipment in need of treatment to control, minimize and/or eliminate algae.

2. Background

Many pools, ponds, lakes, tanks, estuaries, and oceans contain a substantial population of suspended algae in the water body's water column. These algae give the water a greenish and often murky appearance that many observers find unattractive. Floating agglomerations of undesirable filamentous algae also can occur. Algae blooms, where a high concentration of algae are found in a water body, lead to low levels of dissolved oxygen, and stress the aquatic and fish populations. In some cases, such conditions lead to fish kills and decrease the overall quality of a water body.

Currently used methods of controlling algae growth include treating water with algaecides. For example, U.S. Pat. No. 5,407,899 describes copper sulfate used for algae control. Known algaecide agents kill the algae and return the water to a more desired appearance of clear or less colored waters. However, known algaecides are problematic in that they may be costly and potentially toxic to the environment. Moreover, after algaecides dissipate, the use of algaecides has not necessarily altered the water conditions, which remain suitable for subsequent growth of algae, and/or renewed contamination.

Thaxtomins are a known group of phytotoxins, however, although thaxtomin A and analogues thereof demonstrate many of the biological properties desirable in potential herbicides, they are known to lack the systemic phytotoxicity critical to deliver reliable weed control in the field at low herbicide rates. See, for example, *Herbicidal Properties of the Thaxtomin Group of Phytotoxins, J. Agric. Food Chem.*, Vol. 49, No. 5, 2001.

Both algae contamination and the use of algaecides continue to be problematic. Retreating contaminated environments compounds the overall cost of treatment, and increases the potential for toxic accumulation of the algaecide in the environment. Thus, there is a continuing need for new algaecides, and methods of using and making algaecides and formulations thereof. Moreover, there is a continuing need to identify algaecides which may be easily manufactured, and/or less environmentally damaging than known algaecides.

SUMMARY

The present disclosure provides one or more novel algaecides and methods for treating algae by contacting algae with an effective amount of one or more thaxtomins and/or analogues thereof, Non-limiting suitable thaxtomins include thaxtomin A, thaxtomin B, thaxtomin D, derivatives thereof, and combinations thereof. In embodiments, solely, thaxtomin A is used in accordance with the present disclosure.

The present methods are suitable where the algae is in a liquid environment, such as water. Suitable liquid environments include pools, ponds, fish farms, lakes, streams, paddies, rivers, oceans, estuaries, freshwater aquariums, salt water aquariums, aquacultures, tanks for commercial aquaculture, ponds for commercial aquaculture, ornamental ponds, water gardens, run-off streams or ditches and combinations thereof. In embodiments, the algae are in a soil or mud environment. In embodiments, the algae is contaminating containers, tanks, bioreactors or other apparatus used to commercially grow algae, such as algae grown for biofuel or alternative energy purposes.

Methods of controlling, reducing and/or killing algae by contacting algae with thaxtomins, such as thaxtomin A are also disclosed.

In embodiments, the present disclosure relates to a method of treating algae comprising, or consisting of contacting algae with an effective amount of one or more thaxtomins. In embodiments, the one or more thaxtomins include compounds comprising, or consisting of thaxtomin A, thaxtomin B, thaxtomin D, and combinations thereof. In embodiments, the one or more thaxtomins only include thaxtomin A. In some embodiments, the algae is in a liquid environment, such as water. For example, suitable liquid environments include a pool, pond, paddy, lake, stream, river, ocean, estuary, freshwater aquarium, salt water aquarium, tank for commercial aquaculture, pond for commercial aquaculture, ornamental pond, water garden, run-off stream, and combinations thereof. In some embodiments, the algae suitable for treatment are found in a soil or mud environment. In embodiments, treatments include applying an effective amount of thaxtomin such as in an amount where the applied concentration is about 0.5 ppm to about 100 ppm.

In embodiments, the present disclosure provides a method of controlling the growth of algae comprising, or consisting of contacting algae with one or more thaxtomins. In some embodiments, the present disclosure provides a method of killing algae comprising, or consisting of contacting algae with thaxtomin A.

In embodiments, one or more thaxtomins are applied to an area in need of algae control such as a bioreactor, tank, farm equipment, and combinations thereof. In some embodiments, thaxtomin is mixed with a carrier to form a solution having thaxtomin at concentration of about 0.05 ppm to about 500 ppm. Such a solution can be applied to a contaminated surface in need of decontamination or algae reduction or elimination.

As used herein "algae" refers to any of various chiefly aquatic, eukaryotic, photosynthetic organisms, ranging in size from single-celled forms to the giant kelp. The term may further refer to photosynthetic protists responsible for much of the photosynthesis on Earth. As a group, the algae are polyphyletic. Accordingly, the term may refer to any protists considered to be algae from the following groups, alveolates, chloraraachniophytes, cryptomonads, euglenids, glaucophytes, haptophytes, red algae such as Rhodophyta, stramenopiles, and viridaeplantae. The term refers to the green, yellow-green, brown, and red algae in the eukaryotes. The term may also refer to the cyanobacteria in the prokaryotes. The term also refers to green algae, blue algae, and red algae.

As used herein "algaecide" refers to one or more agents, compounds and/or compositions having algaestatic and/or algaecidal activity.

As used herein "algaecidal" as used herein means the killing of algae.

As used herein "algaestatic" as used herein means inhibiting the growth of algae, which can be reversible under certain conditions.

As used herein "lower alkyl" refers to branched or straight chain acyclic alkyl group including one to about eighteen carbon atoms. Exemplary alkyl groups include, inter alia, methyl, ethyl, n-propyl, isopropyl, n-butyl, isobutyl, sec-butyl, pentyl, iso-amyl, hexyl, octyl, decyl, and the like.

As used herein "hydroxy" refers to —OH.

As used herein "H" refers to a hydrogen atom.

As used herein "ppm" refers to parts-per-million.

DETAILED DESCRIPTION OF PREFERRED EMBODIMENTS

*Streptomyces scabies, S. acidiscabies*, and *S. turgidiscabies* are the causative agents of scab disease on a variety of underground potato. A class of phytotoxins, thaxtomin, have been identified therefrom which are involved in the pathogenesis. It has now been found that thaxtomins are suitable for the control, reduction, and/or elimination of algae, including green algae, blue algae, and red algae. Thaxtomins have been found to have algaecidal and algaestatic activity.

The present disclosure provides methods and compositions for treating algae. The methods include applying a predetermined amount of algaecide to an area in need of control or treatment such as an algae contaminated area. The algaecide may be in solution and/or solvated and made available to kill, control and/or minimize algae. In embodiments, the algaecide is in solution, thus is available to penetrate the algae in a bio-effective form.

Suitable algaecides for use in accordance with this disclosure include one or more thaxtomins. Thaxtomins include any of the type from a family of cyclic dipeptides, such as 4-nitroindol-3-yl-containing 2,5-dioxopiperazines commonly known as the thaxtomins. Suitable thaxtomins include agents described as cyclic dipeptides having the basic structure cyclo-(L-4-nitrotryptophyl-L-phenylalanyl). In embodiments, suitable diketopiperazine moieties may be N-methylated, and include congeners carrying phenylalanyl α- and ring-carbon hydroxyl groups. Non-limiting examples of suitable thaxtomins for use in accordance with the present disclosure include thaxtomin A, thaxtomin A ortho isomer, thaxtomin B, and C-14 deoxythaxtomin B (thaxtomin D), and derivatives of any of these. Combinations of thaxtomins and derivatives thereof are also suitable for use in accordance with the present disclosure.

In embodiments, purified thaxtomin and analogues thereof are suitable algaecides for use in accordance with the present disclosure. The chemical compositions include:

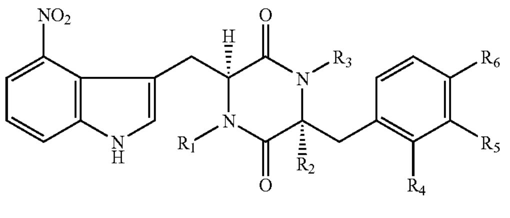

In embodiments, $R_1$ is methyl or H.

In embodiments, $R_2$ is hydroxy or H.

In embodiments, $R_3$ is methyl or H.

In embodiments, $R_4$ is hydroxy or H.

In embodiments, $R_5$ is hydroxy or H.

In embodiments, $R_6$, hydroxy or H.

In embodiments, $R_1$ is methyl, $R_2$ is hydroxy, $R_3$ is methyl, $R_4$ is H, $R_5$ is hydroxy and $R_6$ is H.

In embodiments, $R_1$ is methyl, $R_2$ is hydroxy, $R_3$ is methyl, $R_4$ is hydroxy, $R_5$ is H and $R_6$ is H.

In embodiments, $R_1$ is methyl, $R_2$ is H, $R_3$ is H, $R_4$ is H, $R_5$ is H and $R_6$ is H.

In embodiments, $R_1$ is methyl, $R_2$ is hydroxy, $R_3$ is methyl, $R_4$ is H, $R_5$ is H and $R_6$ is H.

In embodiments, $R_1$ is methyl, $R_2$ is H, $R_3$ is methyl, $R_4$ is H, $R_5$ is H and $R_6$ is H.

In embodiments, $R_1$ is methyl, $R_2$ is hydroxy, $R_3$ is H, $R_4$ is H, $R_5$ is H and $R_6$ is H.

In embodiments, $R_1$ is methyl, $R_2$ is hydroxy, $R_3$ is methyl, $R_4$ is H, $R_5$ is H and $R_6$ is hydroxy.

In embodiments, $R_1$ is methyl, $R_2$ is hydroxy, $R_3$ is methyl, $R_4$ is H, $R_5$ is hydroxy and $R_6$ is hydroxy.

In embodiments, $R_1$ is methyl, $R_2$ is hydroxy, $R_3$ is H, $R_4$ is H, $R_5$ is hydroxy and $R_6$ is H.

In embodiments, $R_1$ is H, $R_2$ is hydroxy, $R_3$ is methyl, $R_4$ is H, $R_5$ is hydroxy and $R_6$ is H.

In embodiments, $R_1$ is H, $R_2$ is H, $R_3$ is H, $R_4$ is H, $R_5$ is H and $R_6$ is H.

In embodiments, purified thaxtomin A is a suitable algaecide for use in accordance with the present disclosure. Thaxtomin A is a yellow compound composed of 4-nitroindol-3-yl-containing 2,5-dioxopiperazine and is the predominant thaxtomin produced by *Streptomyces scabies, Streptomyces acidiscabies*, and *Streptomyces turgidiscabies*, with phenylalanyl m-ring and α-C hydroxyl additions. The chemical composition comprises, or consists of:

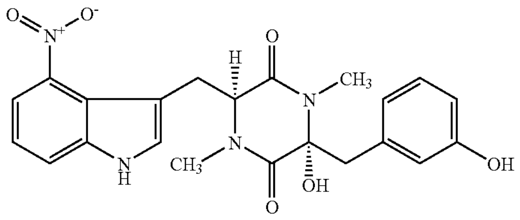

The mode of action of thaxtomin on algae is not known. However, not wishing to be bound by the present disclosure it is believed thaxtomins when contacted with algae inhibit cellulose biosynthesis.

In embodiments, unpurified supernatant from cell cultures such as cell cultures of *Streptomyces scabies, Streptomyces acidiscabies*, and *Streptomyces turgidiscabies* containing one or more thaxtomin(s) is suitable for use as an algaecide in accordance with the present disclosure. One of ordinary skill in the art would readily envision that supernatant is readily obtainable from cell cultures, such as through centrifugation and collection of the remaining liquid portion.

In embodiments, one or more thaxtomins can be applied to algae contaminated environments to control, minimize and/or eliminate undesirable algae. As used herein the word "treat," "treating" or "treatment" refers to using the thaxtomins of the present disclosure prophylactically to prevent outbreaks of undesirable or high algae blooms, or to ameliorate an existing algae contamination. A number of different treatments are now possible, which control, reduce and/or eliminate algae.

As used herein "algae contamination" refers to any detectable algae manifestation(s) caused by one or more algae. Such manifestations can be caused by a number of factors such as, for example, water column nutrient levels, and/or other stressed or dysfunctional environmental states. Non-limiting examples of such manifestations include the development of algae growths, algae scum formation, low levels of dissolved oxygen in a water body, stress on aquatic and fish populations, and/or other forms of reduced environmental quality. It is understood, that the environmental conditions are non-limiting and that only a portion of the environmental conditions suitable for treatment in accordance with the present disclosure are listed herein. Further, algae contamination may also refer to residual algae left over on algae growing apparatuses and equipment such as those used to make algae oil for alternative energy production. Non-limiting examples of equipment and various apparatus that can be cleaned in accordance with the present disclosure include items described in U.S. Pat. Nos. 5,088,231, 5,171,683, 4,978,505, 4,908,315 (each herein incorporated by reference in their entirety). Farm equipment and bioreactors used to grow algae for commercial purposes can be cleaned using the algaecide in accordance with the present disclosure.

In embodiments, compositions for use in accordance with the present disclosure contain one or more thaxtomins in an effective amount to improve water conditions. As used herein "effective amount" refers to an amount of thaxtomin or compound(s) or composition(s) having thaxtomin constituents in accordance with the present disclosure sufficient to induce a particular positive benefit to environmental conditions such as water conditions or conditions considered contaminated or soiled with algae. The positive benefit can be cosmetic in nature, or health-related, or a combination of the two. In embodiments, the positive benefit is achieved by contacting a contaminated environment, area, or apparatus with one or more thaxtomins, and/or one or more thaxtomin constituents, to improve conditions such as algae bloom or algae contamination. Treatments include contacting algae contaminated environments or soiled equipment with an amount of thaxtomin effective to be algaecidal and/or algaestatic.

The particular thaxtomin concentration applied generally depends on the purpose for which the composition is to be applied. For example, the dosage and frequency of application can vary depending upon the type and severity of the algae condition. In embodiments, one or more thaxtomins are applied to a water body such that the thaxtomin concentration is in an amount of 1 ppm to 5 ppm. In embodiments, one or more thaxtomins are applied to a water body such that the thaxtomin concentration is applied in an amount of about 0.5 ppm to 100 ppm. In embodiments, thaxtomin is mixed with a carrier (such as water) in an amount of about 0.05 ppm to 500 ppm and applied to a contaminated area or algae soiled equipment.

Treatments in accordance with the present disclosure contact algae D contaminated areas and/or equipment with one or more thaxtomins in an effective amount to improve algae related conditions. In embodiments, areas in need of treatment or algae control such as pools, ponds, paddies, fish farms, lakes, estuaries, oceans, freshwater aquariums, salt water aquariums, tanks for commercial aquaculture, ponds for commercial aquaculture, ornamental ponds, water gardens, alternative fuel manufacturing equipment or apparatuses, run-off ditches, house sidings, and deck planks are treated by applying to these areas, one or more thaxtomin compositions. The active thaxtomin ingredient is applied until the treatment goals are obtained. However, the duration of the treatment can vary depending on the severity of the condition. For example, treatments can last several days to weeks depending on whether the goal of treatment is to control, reduce and/or eliminate algae contamination.

In embodiments, thaxtomins may be combined with a solvent vehicle to make a formulation for the treatment of algae in which the major active ingredient is one or more thaxtomins. In embodiments, the active ingredients are provided in suspensions, dry form(s), and aqueous solutions. The amount of thaxtomin mixed with the solvent will vary depending on a number of factors, including, for example, the activity of thaxtomin, the type of thaxtomin selected, the ultimate form of the product and the particular disclosed solvent employed. Generally, the thaxtomin constituent will constitute from 1 to 95 weight percent of the thaxtomin/solvent mixture. In embodiments the thaxtomin constitutes from about 10.00 to about 80 weight percent of the thaxtomin/solvent mixture. Solvents useful for preparing the present thaxtomin compositions include any solvent capable solubilizing one or more thaxtomins. Non-limiting examples of such solvents include water and/or aqueous solutions.

In embodiments, thaxtomins may be combined with a dry excipients to make a formulation for the treatment of algae in which the major active ingredient is one or more thaxtomins. In embodiments, the active ingredients are provided in dry form. The thaxtomin constituent will constitute from 1 to 95 weight percent of the thaxtomin dry formulation. In embodiments, the thaxtomin constitutes from about 10.00 to about 80 weight percent of the thaxtomin dry formulation.

The following non-limiting examples further illustrate compositions, methods, and treatments in accordance with the present disclosure. It should be noted that the disclosure is not limited to the specific details embodied in the examples.

Example 1

Supernatant of *Streptomyces acidiscabies* is effective to control or reduce the following green algae: *Oedogonium foveolatum, Spirogyra* spp. *Voavox aureus, Volvox globator, Closterium* sp. *Chlamydomonas* sp. in as low as a 100 fold dilution.

*Streptomyces acidiscabies* was grown in Oat Meal Broth liquid medium at room temperature for 5 days. Cell culture was centrifuged and the supernatant was collected, filtered through a 0.45 μm filter, and saved for bioactivity assay. The supernatant was evaluated against above-mentioned algae at various dilutions. The algae were obtained from Carolina Biological Supply Company and were grown and maintained according to the supplied manual. Alga-Cro Freshwater Medium from Carolina Biological Supply Company was used for growing algae. Maximum Dilution for Inhibition (MDI) was used to measure the activity of the supernatant to algae. The assay was run for 3 weeks. Algae growth was visibly inhibited by that diluted supernatant. Stronger inhibition is expected using more concentrated solutions. Tested results are summarized as follows:

TABLE 1

| TESTED ORGANISM | Maximum Dilution for Inhibition (MDI) |
|---|---|
| *Spirogyra* sp. | ≧100 (greater than 100 fold dilution) |
| *Oedogonium foveolatum* | ≧100 |
| *Closterium* sp. | ≧50 |
| *Chlamydomonas reinhardtii* | ≧10 |
| *Volvox aureus* | ≧10 |
| *Navicula* sp. | ≧0 |
| *Oscillatoria* sp. (Blue-green, filamentous alga) | ≧50 |

Example 2

The supernatant of *Streptomyces acidiscabies* was demonstrated to be toxic to blue-green algae, Blue-green algae (*Oscillatoria* sp) was obtained from Carolina Biological Supply Company and grown in a recommended medium (Alga-Cro Freshwater Medium). The supernatant of *S. acidiscabies* was added into the culture of Algae at various dilutions. The treated algae culture was incubated at room temperature under the regular room light. Three weeks later, algae growth was evaluated in terms of growth inhibition. The results showed the maximum dilution for inhibition for this blue-algae growth is greater than 50 fold.

Example 3

The supernatant of *Streptomyces acidiscabies* was demonstrated to be toxic to red algae: *Batrachospermum* sp., *Callithamnion* sp., and *Rhodymenia* sp. were obtained from Carolina Biological Supply Company. Algae growth and maintenance were based on the supply manual. The protocol used for the bioassay was same as above mentioned. The results from the following table proved that some red algae such as *Batrachospentnum* spp. and *Rhodymenia* spp. were also quite sensitive to thaxtomin supernatant.

TABLE 2

| Tested organism | Maximum Dilution for Inhibition (MDI) |
|---|---|
| *Batrachospermum* spp. | ≧30 |
| *Rhodymenia* spp. | ≧10 |
| *Callithamnion* spp. | ≦10 |

Example 4

*Streptomyces acidiscabies* secreted thaxtomins during the growth under Oat Bran Meal medium.

To confirm that thaxtomins are involved in killing of algae, a negative thaxtomin production mutant was obtained from Cornell University and used as a negative control. Wild type strain and the negative mutant were grown in oat bran liquid medium at 25° C. and their supernatants used for bioassay against the algae in Table 3. The results are show the tested algae were greatly inhibited by the supernatant from wild type strain at more that 10 to 100 fold dilution. However, the supernatant from thaxtomin negative mutant showed no visible inhibition to the tested organisms.

TABLE 3

| Tested Organisms | MDI from wild type supernatant | MDI from mutant supernatant |
|---|---|---|
| *Oedogonium* spp. | ≧100 | 0 |
| *Spirogyra* spp. | ≧100 | 0 |
| *Oscillatoria* spp. | ≧50 | 0 |
| *Batrachospermum* spp. | ≧30 | 0 |
| *Rhodymenia* spp. | ≧10 | 0 |

Example 5

Purified thaxtomin was used for a bioassay test and its efficacy evaluated and compared with copper sulphate, an active ingredient for many copper based algaecides. The bioassay was run for two weeks and inhibition of algae growth was evaluated. The results are in the table below. It was concluded that as low as 1 ppm of purified thaxtomin was effective to control, and kill the tested algae. However 2 ppm of cupper sulfate (commercial recommended rate for cupper sulfate) was not very effective against the tested organisms in our assay system.

TABLE 4

Bioactivity of purified thaxtomin verse CuSO4

| Tested organisms | Thaxtomin (1 ppm) | CuSO4(2 ppm) |
|---|---|---|
| *Oedogonium* spp. | ++ | − |
| *Spirogyra* spp. | ++ | + |
| *Oscillatoria* spp. | + | − |
| *Batrachospermum* spp. | + | − |
| *Rhodymenia* spp. | + | − |

Note;

++ = visible death;

+ = growth inhibition;

− = no visible growth inhibition.

Example 6

Thaxtomin was effective to control algae in a minipond ecosystem. To demonstrate effectiveness of using thaxtomin to control an algae problem, a minipond ecosystem was obtained from Carolina Biological Supply Company (13-1207). The system included an algae mixture (*Oedogonium, Volvox, Chlamydomonas*) and a protozoan mixture (*Amoeba, Paramecium, Euglena, Stentor, Volvox*, and *Chilomonas*). The minipond ecosystems were set up based on the supplied manual. Next, a 20 fold dilution of fermented thaxtomin supernatant was applied to the pond system A 2 ppm CuSO4 solution and water were applied to identical systems as positive control and negative control respectively. Three months later, algae growth was evaluated. The results are shown in Table 5.

TABLE 5

| Sample | Results |
|---|---|
| Minipond w/algae and protozoan mixtures after 3 months. | Pond is light brown, and has clear water. No visible green algae growth in the thaxtomin treated pond system. |
| Positive Control ($CUSO_4$ Solution) after 3 months | Pond dark green with reasonable green algae growth. |
| Negative Control (Water solution) after three months. | Pond is bright green with large amount of algae growth. |

Example 7

Thaxtomin was demonstrated to possess very high activity at low concentration in controlling the growth of a wide variety of algae. Thaxtomin was added to water and algae in a test tube.

TABLE 6

| | Constituents | Prior to Treatment-Characteristics of water and algae mix | Results (after contact with thaxtomin) |
|---|---|---|---|
| Control Group | 2 ml water and algae (mix) | Distinct bright green algae. | No change, distinct bright green algae suspended in solution. |
| Treatment 1 | Thaxtomin was added to 2 ml water and algae mix (thaxtomin concentration 0.5 ppm) | Distinct bright green algae. | Significant changes including the reduction in visible algae in solution. Algae killed resulting in appearance of yellow and brown colored (dead) algae. A 10 fold reduction in algae is observed. Some green algae was still present in the solution. |
| Treatment 2 | 10 mMol (2,840 ppm) of Metolachlor was applied to 2 ml water and algae mix. | Distinct bright green algae. | No change, distinct bright green algae suspended in solution. |

Metolachlor (2-chloro-N-(6-ethyl-o-tolyl)-N-[(1RS)-2-methoxy-1-methylethyl]acetamide) is a known pre-emergent herbicide commonly used to control annual grasses and some broadleaves such as Eastern black nightshade and pigweeds. At concentrations effective in terrestrial weed control (10 mMol), Metolachlor did not show any algaestatic and/or algaecidal activity. Conversely, thaxtomin was very effective in controlling green algae at a dose of only 0.5 ppm, much lower than the concentration needed to control terrestrial weeds (5-10 ppm).

Example 8

Thaxtomin was show to possess very high activity at low concentration in controlling the growth of various algae. Further, selective control of algae was shown without harming existing aquatic plants.

Mondo grass, Water Onion and Cabomba were obtained from a local aquarium store and planted in three 2.5 L fish tanks. Each tank was treated as follows:

Tank 1: Thaxtomin applied at a final concentration of 20 ppm (45 µMol).

Tank 2: Glyphosate (Roundup®) was applied at a concentration of 169 ppm (1 mM, the normal dose used for aquatic weed control).

Tank 3: Untreated (Control tank)

Tanks 1, 2 and 3 were monitored for 3 weeks. The results are shown in Table 7 below:

TABLE 7

| | Description after 3 weeks |
|---|---|
| Tank 1 | No visible plant damage was observed. Algae was controlled. |
| Tank 2 | Most of the plants were dead. |
| Tank 3 | No visible plant damage was observed. |

This test demonstrated that Thaxtomin demonstrates selective control of algae at a low concentration which have no effect on existing aquatic plants.

Example 9

A pool of agricultural waste runoff has algae growing throughout the water body of the pool. The algae is unsightly and unattractive. A predetermined effective amount of thaxtomin A is added to the pool to kill the algae. The algae is expected to die and the pool is expected to be cleaner.

Example 10

A child owns an aquarium including tropical fish. The aquarium becomes contaminated with algae which are visible as a scum on the glass walls of the aquarium. One or more thaxtomins is added to the aquarium to kill the algae. The walls are expected to clear and the algae contamination is expected to subside.

Example 11

An aquarium susceptible to algae growth is prophylactically treated by adding thaxtomins to the tank. Algae contamination is expected to be prevented.

Example 12

Thaxtomin and thaxtomin compositions in accordance with the present disclosure are applied to the siding and deck planks of a house. Algae contamination is expected to be prevented for up to 2-6 months.

Example 13

Thaxtomin and thaxtomin compositions in accordance with the present disclosure are applied to fish farm waters. Algae contamination is expected to be prevented for up to 2-6 months.

Example 14

Thaxtomin in accordance with the present disclosure is added to a water carrier solution to a concentration of 100 ppm. The solution is sprayed onto soiled algae bioreactors used to create algae for the production of biofuel. The bioreactors are expected to become clean and unsoiled.

Example 15

Thaxtomin in accordance with the present disclosure is applied to a lawn or golf green which is contaminated with algae growth. The lawn or green is expected to lose the algae contamination, with little or no harm to existing grasses.

It will be understood that various modifications may be made to the embodiments disclosed herein. Therefore, the above description should not be construed as limiting, but merely as exemplifications of embodiments. Those skilled in art will envision other modifications within the scope and spirit of the claims appended hereto.

What is claimed is:

1. A method of treating algae comprising contacting algae with an effective amount of one or more thaxtomins.

2. A method in accordance with claim 1, wherein the one or more thaxtomins are selected from the group consisting of thaxtomin A, thaxtomin B, thaxtomin D, and combinations thereof.

3. A method in accordance with claim 1, wherein the one or more thaxtomins comprise thaxtomin A.

4. A method in accordance with claim 1, wherein the algae is in a liquid environment.

5. A method in accordance with claim 4 wherein the liquid environment is water.

6. A method in accordance with claim 4 wherein the liquid environment is a pool, pond, paddy, lake, stream, river, ocean, estuary, freshwater aquarium, salt water aquarium, tank for commercial aquaculture, pond for commercial aquaculture, ornamental pond, water garden, or a combination thereof.

7. A method in accordance with claim 1, wherein the algae is in a soil or mud environment.

8. A method in accordance with claim 1, wherein the effective amount is an amount where the applied concentration is about 0.5 ppm to about 100 ppm.

9. A method of controlling the growth of algae comprising contacting algae with one or more thaxtomins.

10. A method of killing algae comprising contacting algae with thaxtomin A.

11. A method of controlling algae by applying one or more thaxtomins to an area in need of algae control.

12. The method of claim 11 wherein the area in need of control is a house, a fish farm, pool, pond, lake, stream, river, ocean, estuary, freshwater aquarium, salt water aquarium, tank for commercial aquaculture, pond for commercial aquaculture, ornamental pond, or water garden, or a combination thereof.

13. The method of claim 11, wherein the one or more thaxtomins has the following composition:

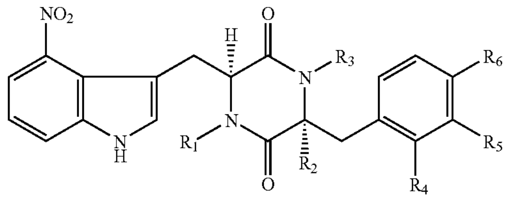

wherein $R_1$ is methyl or H, $R_2$ is hydroxy or H, $R_3$ is methyl or H, $R_4$ is hydroxy or H, $R_5$ is hydroxy or H, $R_6$ is hydroxy or H, or a combination thereof.

14. The method according to claim 13 wherein $R_1$ is methyl, $R_2$ is hydroxy, $R_3$ is methyl, $R_4$ is H, $R_5$ is hydroxy and $R_6$ is H.

15. The method of claim 11 wherein the area in need of control is a bioreactor, a tank, farm equipment, or a combination thereof.

16. The method in accordance with claim 11, wherein the one or more thaxtomins is mixed with a carrier to form a solution having the one or more thaxtomins at a concentration of about 0.05 ppm to about 500 ppm.

17. The method in accordance with claim 16, further comprising applying the solution to a contaminated surface.

* * * * *